United States Patent
Minami et al.

(10) Patent No.: US 11,879,863 B2
(45) Date of Patent: Jan. 23, 2024

(54) METHOD FOR ANALYZING LIQUID SAMPLE AND APPARATUS

(71) Applicant: NATIONAL INSTITUTE FOR MATERIALS SCIENCE, Ibaraki (JP)

(72) Inventors: Kosuke Minami, Ibaraki (JP); Genki Yoshikawa, Ibaraki (JP)

(73) Assignee: NATIONAL INSTITUTE FOR MATERIALS SCIENCE, Ibaraki (JP)

( * ) Notice: Subject to any disclaimer, the term of this patent is extended or adjusted under 35 U.S.C. 154(b) by 456 days.

(21) Appl. No.: 17/289,394

(22) PCT Filed: Nov. 13, 2019

(86) PCT No.: PCT/JP2019/044474
§ 371 (c)(1),
(2) Date: Apr. 28, 2021

(87) PCT Pub. No.: WO2020/110720
PCT Pub. Date: Jun. 4, 2020

(65) Prior Publication Data
US 2021/0396699 A1 Dec. 23, 2021

(30) Foreign Application Priority Data
Nov. 26, 2018 (JP) ................. 2018-220427

(51) Int. Cl.
*G01N 27/12* (2006.01)
*G06N 20/00* (2019.01)

(52) U.S. Cl.
CPC ............. *G01N 27/12* (2013.01); *G06N 20/00* (2019.01)

(58) Field of Classification Search
CPC ............... G01N 27/12; G01N 29/4481; G01N 2291/02466; G01N 2291/0256;
(Continued)

(56) References Cited

U.S. PATENT DOCUMENTS

| 11,391,687 B2* | 7/2022 | Yoshikawa ........ G01N 33/0031 |
| 2013/0062523 A1* | 3/2013 | Chernokalskaya ... G01J 5/0255 73/864.91 |

(Continued)

FOREIGN PATENT DOCUMENTS

| CN | 108369218 | 8/2018 |
| EP | 3 080 294 | 10/2016 |

(Continued)

OTHER PUBLICATIONS

Extended European Search Report dated Jul. 6, 2022 in corresponding European Patent Application No. 19 88 9567.4.
(Continued)

*Primary Examiner* — Freddie Kirkland, III
(74) *Attorney, Agent, or Firm* — WENDEROTH, LIND & PONACK, L.L.P.

(57) ABSTRACT

The present invention provides a method for analyzing a liquid sample that solves a problem of a kinetically slow equilibrium at a liquid-solid interface, the problem occurring when liquid sample analysis is performed with a chemical sensor. In the method for analyzing a liquid sample according to an embodiment of the present invention, a component to be analyzed in a liquid sample is adsorbed on a receptor layer of a chemical sensor, one or more kinds of gases are then supplied to the chemical sensor, and a response thereof is measured. As a result, since a slow equilibrium at a liquid-solid interface is not used, a high-sensitivity measurement can be performed in a short time, and existing findings regarding analysis of gas samples on which much progress in research has been achieved can be used.

13 Claims, 5 Drawing Sheets

(58) Field of Classification Search
CPC ......... G01N 2291/0257; G01N 29/022; G01N 33/48707; G01N 33/54373; G06N 20/00
See application file for complete search history.

(56) References Cited

U.S. PATENT DOCUMENTS

| | | |
|---|---|---|
| 2013/0133433 A1 | 5/2013 | Yoshikawa et al. |
| 2018/0003604 A1* | 1/2018 | Shiba .................. G01G 3/13 |
| 2018/0356388 A1 | 12/2018 | Shiba et al. |
| 2019/0323982 A1 | 10/2019 | Yoshikawa et al. |
| 2020/0075134 A1 | 3/2020 | Shiba et al. |

FOREIGN PATENT DOCUMENTS

| | | |
|---|---|---|
| EP | 3 208 597 | 8/2017 |
| WO | 2011/148774 | 12/2011 |
| WO | 2018/079509 | 5/2018 |
| WO | 2018/101128 | 6/2018 |

OTHER PUBLICATIONS

International Search Report (ISR) dated Jan. 28, 2020 in International (PCT) Application No. PCT/JP2019/044474.
Genki Yoshikawa, et al., "Two Dimensional Array of Piezoresistive Nanomechanical Membrane-Type Surface Stress Sensor(MSS) With Improved Sensitivity", Sensors, 12, pp. 15873-15887, 2012, cited in the specification.
Office Action dated Jul. 13, 2023 in the correponding Chinese Patent Application No. 201980077729.X, with English translation.
Communication pursuant to Article 94(3) dated Mar. 10, 2023 in corresponding European Patent Application No. 19889567.4.

* cited by examiner

METHOD FOR ANALYZING LIQUID SAMPLE AND APPARATUS

TECHNICAL FIELD

The present invention relates to liquid sample analysis, and particularly to a method for analyzing liquid sample to which a method for analyzing gas sample with a chemical sensor such as a surface stress sensor is applied. The present invention also relates to an apparatus for analyzing liquid sample that performs analysis by this analyzing method.

BACKGROUND ART

For example, in fields such as medicine and biology, a sample is often identified or analyzed. In such a case, as a target sample, not only a gaseous sample but also a liquid sample is often used. However, there is difficulty different from that of a gas in identifying or analyzing the liquid sample. Currently used many biosensors detect a target specimen on a one-to-one basis, for example, detect a target specimen with an antigen-antibody reaction. In such a detection modality, it is necessary to detect a biomarker having a very low concentration, and therefore it is necessary to detect each of known biomarkers. Therefore, it is necessary to perform detection using a large number of sensors with very high sensitivity. For this reason, such a liquid sample analysis apparatus is large and expensive, and has hardly been put into practical use as a product for the general public.

A method for identifying or quantifying a specimen using a chemical sensor that indicates respective specific responses to various substances has been developed. A chemical sensor has attracted much attention as a powerful tool for detecting, distinguishing, and identifying a target specimen, particularly various odors formed of complicated mixtures of gaseous molecules. This type of sensor generally detects a change in a physical parameter caused by adsorption of a detection target molecule (specimen molecule). In order to easily detect the change in a physical parameter, the sensor is generally coated with a layer called a "receptor layer" and then used for a measurement. Note that in the present application, the sensor before being coated with the receptor may be referred to as a sensor body. The physical parameters detected by this type of sensor are diverse, but non-limiting examples thereof include surface stress, stress, force, surface tension, pressure, mass, elasticity, Young's modulus, Poisson's ratio, resonance frequency, frequency, volume, thickness, viscosity, density, magnetic force, magnetic quantity, magnetic field, magnetic flux, magnetic flux density, electric resistance, electric quantity, dielectric constant, electric power, electric field, charge, current, voltage, potential, mobility, electrostatic energy, capacitance, inductance, reactance, susceptance, admittance, impedance, conductance, plasmon, refractive index, luminous intensity, temperature, and a combination thereof. Specific examples of the chemical sensor include various sensors such as a quartz crystal microbalance (QCM), a conductive polymer (CP), and a field effect transistor (FET). Such a chemical sensor may be used as a single sensor, but in many cases, has been used as a chemical sensor array obtained by collecting a plurality of sensor elements (hereinafter, also referred to as channels) into an array in some form.

However, so far, the number of examples of liquid sample analysis with a chemical sensor is smaller than that of gaseous sample analysis. In particular, little research has been performed on liquid sample analysis using a pattern recognition method. One of factors for this is that it is difficult to obtain an effective signal pattern with a kinetically slow equilibrium at a liquid-solid interface. On the other hand, for a gaseous sample, an equilibrium at a gas-solid interface is significantly faster than that for a liquid, indicating that pattern recognition is an effective method.

SUMMARY OF INVENTION

Technical Problem

Recently, the inventors of the present application have found that pattern recognition based on a gas-solid interface can be further extended to a method of reverse direction, that is, solid sample recognition. As a proof of concept, an example of distinguishing among various solid layers coated on a chemical sensor represented by a nanomechanical sensor was indicated, and as illustrated in FIG. 4, it was confirmed that this method makes it possible to clearly recognize a very slight difference between solid layers. Therefore, if a liquid sample can be extracted and immobilized in a solid matrix (sometimes referred to simply as a matrix), by applying pattern recognition effectively to liquid analysis via a gas-solid interface, pattern recognition of the liquid sample can be achieved. Of course, the present invention is useful even when a necessary analysis result can be obtained visually or by another simple method without applying pattern recognition or the like to the result.

Therefore, an object of the present application is to perform liquid sample analysis with high accuracy using a chemical sensor. Another object of the present application is to achieve analysis with higher accuracy by applying a statistical process, pattern recognition, and the like to such liquid sample analysis.

Solution to Problem

An aspect of the present invention provides a method for analyzing a liquid sample, the method comprising, providing a chemical sensor with a receptor layer supported thereon, supplying the liquid sample to be measured to the chemical sensor, supplying one or more kinds of gases to the chemical sensor after supplying the liquid sample, and analyzing a component in the liquid sample to be measured based on a signal output from the chemical sensor exerted by a change in a physical parameter due to supply of the one or more kinds of gases to the chemical sensor.

The receptor layer may be dried before the one or more kinds of gases are supplied to the chemical sensor.

The physical parameter may be one or more selected from a group consisting of surface stress, stress, force, surface tension, pressure, mass, elasticity, Young's modulus, Poisson's ratio, resonance frequency, frequency, volume, thickness, viscosity, density, magnetic force, magnetic quantity, magnetic field, magnetic flux, magnetic flux density, electric resistance, electric quantity, dielectric constant, electric power, electric field, charge, current, voltage, potential, mobility, electrostatic energy, capacitance, inductance, reactance, susceptance, admittance, impedance, conductance, plasmon, refractive index, luminous intensity, and temperature.

The physical parameter may be surface stress.

The chemical sensor may be a membrane-type surface stress sensor.

The receptor layer may comprise a material selected from a group consisting of a polymer, an organic compound other than the polymer, an inorganic compound, a simple substance material, a porous body, and an aggregate of particles.

The analysis may be performed based on a result of extracting a feature value from the signal output from the chemical sensor.

The gas and a purging fluid may be alternately supplied to the chemical sensor.

The component in the liquid sample to be measured may be analyzed by subjecting the signal output from the chemical sensor to machine learning.

The component in the liquid sample to be measured may be analyzed by subjecting the signal output from the chemical sensor to multivariate analysis.

The component in the liquid sample to be measured may be analyzed by applying principal component analysis or linear discriminant analysis to the signal output from the chemical sensor.

The component in the liquid sample to be measured may be analyzed by applying pattern recognition to the signal output from the chemical sensor.

Another aspect of the present invention provides an apparatus for analyzing a liquid sample comprising a chemical sensor, and means for analysis that analyzes a signal output from the chemical sensor so that the apparatus for analyzing a liquid sample performs any one of the above methods for analyzing a liquid sample.

Advantageous Effects of Invention

The present invention performs liquid sample analysis by diverting gas analysis with a chemical sensor, and therefore can achieve analysis with high accuracy and large distinguishing ability for a liquid sample.

DESCRIPTION OF EMBODIMENTS

In the present invention, liquid sample analysis is performed using a chemical sensor such as a nanomechanical sensor. By performing a part of a process of the analysis in a gas phase instead of performing the analysis consistently in a liquid phase as in prior art, the present invention solves the above-described problem caused by a slow equilibrium at a liquid-solid interface. Note that the "liquid sample" referred to in the present application is a sample that is liquid at the time when the sample is supplied to a chemical sensor. Various components are, for example, dissolved and dispersed in the liquid sample. The liquid sample may change to solid or gas depending on conditions, for example, the whole liquid sample or some components of the liquid sample may be solidified, or volatile components thereof may become gas due to a change in the temperature of the sample, addition of other substances, evaporation of volatile components, passage of time, and the like. However, it should be noted that in the present application, even a sample the whole or a part of which may be in a state other than liquid due to a change in conditions and the like can be regarded as a liquid sample if the sample is liquid at the time when the sample is supplied to a chemical sensor.

Chemical sensors having various types and structures have been reported so far, and a chemical sensor can be appropriately selected from these chemical sensors for use. In the following description, Membrane-type Surface stress Sensors (hereinafter referred to as MSS) are used as an example of the chemical sensor. The specific structure, manufacturing method, operation, properties, and the like of the MSS are well-known and are not specifically described in the present application, but refer to Patent Literature 1, Non Patent Literature 1, and the like as necessary. A material of a receptor, the form of its coating, and the like are appropriately designed and selected depending on a purpose of analysis, a sample to be analyzed, and the like.

Figure 1:
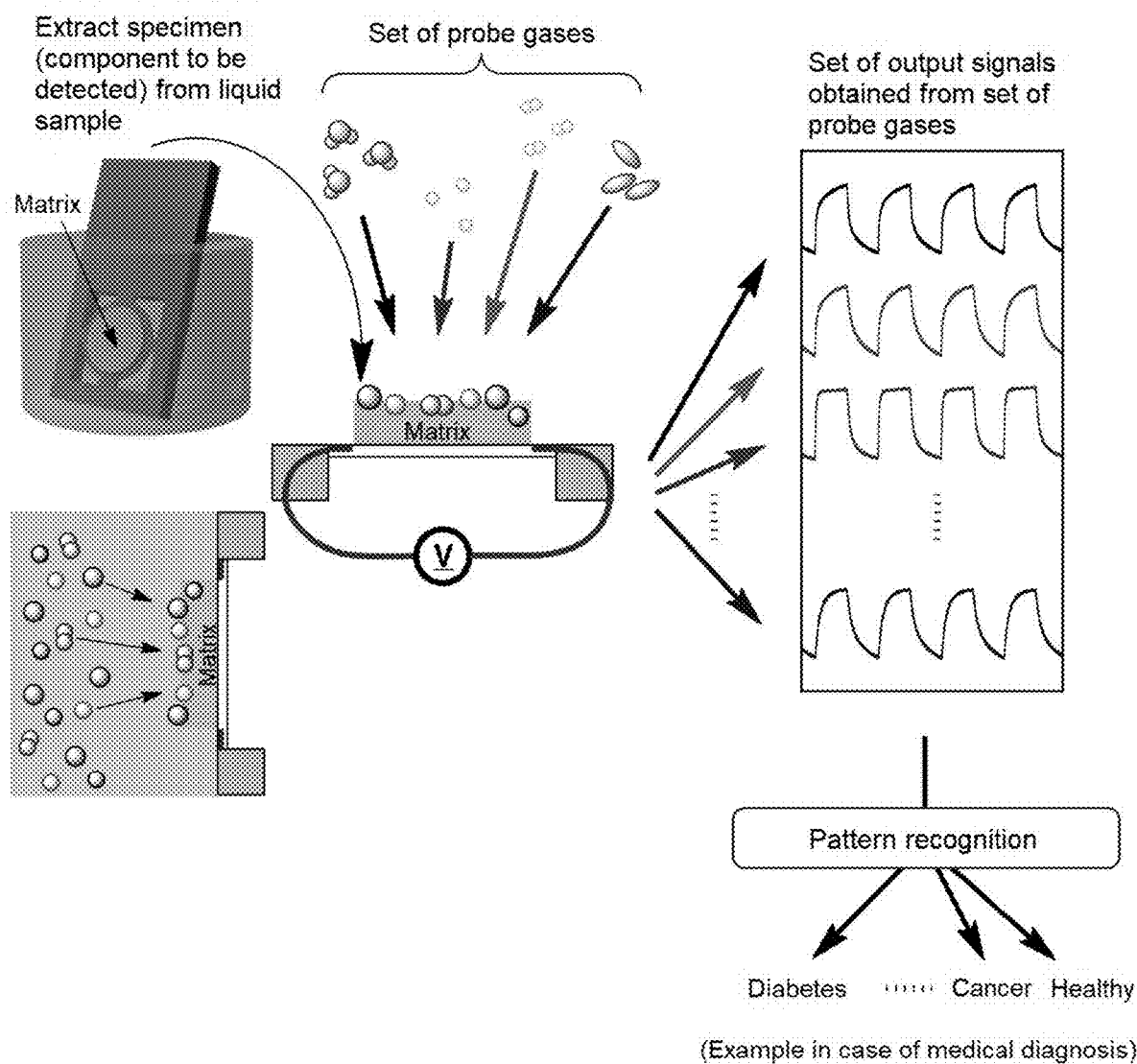
FIG. 1 is a conceptual diagram for explaining a process of liquid sample analysis according to the present invention.

According to an embodiment of the present invention, liquid sample analysis is performed as conceptually illustrated in FIG. 1. In the first half of a measurement process, for example, by immersing an MSS in which a top surface of a sensor body is coated with a receptor material in a liquid sample, the liquid sample is supplied to the MSS. As a result, various components in the liquid sample are bonded to the solid receptor on the surface of the MSS by adsorption or the like.

In the second half of the measurement process, the MSS to which various components in the liquid sample are bonded as described above is withdrawn from the liquid sample and then dried. After the MSS is dried, an appropriate gas (hereinafter referred to as a probe gas) is supplied to the MSS to obtain an output signal from the MSS. This output signal contains a pattern of signals reflecting a unique interaction between the supplied probe gas and the various components bonded to the MSS receptor. When a liquid sample component to be analyzed provides a very characteristic output signal that can be easily distinguished for a combination of a particular receptor with a particular probe gas, the component can be, for example, identified and quantified by a simple method such as visual observation of the output signal or simple pattern matching. However, in many cases, as illustrated in FIG. 1, more precise and accurate results can be obtained by, for example, identifying and quantifying the liquid sample component or the liquid sample itself by using a plurality of receptors and/or a plurality of probe gases to obtain response signals for these combinations, and subjecting these response signals to pattern recognition or the like as necessary.

Note that various methods other than immersing the MSS in the liquid sample can be used for supplying the liquid sample to the MSS. Although it is not intended to limit to these, if it is listed in a non-limiting manner, it is also possible to supply the liquid sample to the MSS in a form of droplets, for example, by dropping or spraying the liquid sample. Although it is described above that the liquid sample is supplied to the MSS and then the MSS is dried, it is not necessary to perform this drying until a solvent is completely removed, and a drying treatment may be discontinued and a subsequent measurement may be performed in a state in which the solvent remains partially, in an extreme case, in a semi-dried state, that is, in a state in which it is clearly found that the solvent remains even by visual observation or other simple observation. Furthermore, in the above description, it may be understood that a measurement of supplying a probe gas and observing an output signal from the MSS is not performed until an end of drying. However, actually, it is not intended to be limited to such a case, and an output signal can also be obtained while the probe gas is supplied even in the drying process as necessary. Another treatment may be performed as necessary before and after the drying treatment, that is, between the supply of the liquid sample and the drying and/or after the drying. Examples of such a treatment include a cleaning treatment for removing an excess amount of the liquid sample and the like adhering to the surface of the MSS, and other various treatments for stabilizing the adsorption state of a liquid sample component adsorbed on the receptor or affecting measurement sensitivity.

The pattern recognition in the present application does not mean pattern recognition in a narrow sense limiting a target to geometric figures but is to determine a class to which each data set (which can be expressed as a data vector in a case of digital data) belongs from features of the data set as used in many data processing fields. For example, in a case of output of one MSS, the output is usually sampled and digitized. The entire series of digital data is one data set, and the entire data sets obtained from a large number of samples form a data set space. This data set space is divided into a plurality of classes, and a class to which a data set obtained from a certain measurement belongs is determined. For example, by dividing a data set space formed by data sets obtained by measuring blood into classes according to a corresponding disease (∘∘ cancer, □□ cancer, . . . , diabetes, . . . ), and determining a class to which a data set obtained from a measurement of a particular blood sample belongs, it is possible to analyze blood, such as determining a disease which the blood donor may be suffering from. Here, a pattern recognition method to be used may be appropriately selected depending on the type of sample to be measured, the type of receptor, other measurement conditions, and various characteristics of a data set of measurement results.

Note that in the present application, various statistical processes that express the degree of similarity between data sets in some form based on the features of the data sets, such as principal component analysis (PCA) and linear discriminant analysis (LDA), and machine learning related thereto are also included in pattern recognition.

The analysis described above can be applied, for example, as illustrated in FIG. 1, to the diagnosis and screening of a disease such as cancer or diabetes in a medical diagnosis field, of course, although the application field is not limited thereto.

When a plurality of kinds of receptors is prepared and a plurality of MSS elements is coated with the receptors to obtain a set of response signals of the plurality of kinds of receptors for one liquid sample, in an MSS, it is easy to form a plurality of MSS elements having uniform characteristics on one sensor chip, and it is convenient because such an MSS is actually manufactured. When viewed as a measurement system, each of these MSS elements (usually coated with different receptors) is hereinafter referred to as a channel. By using an MSS having a plurality of channels, it is possible to easily obtain a set of response signals of a plurality of kinds of receptors for a single liquid sample as described above. Of course, when response signals from a very large number of channels are required, a plurality of MSS may be used at the same time. The response signals are usually digitized and then used for display, storage, data processing, and the like.

In addition to the method for preparing a plurality of MSS and supplying a single type of probe gas to the MSS, it is also possible to perform analysis using a single (or less than the kinds of probe gases) MSS. In such a case, for example, after an end of a cycle in which one of various kinds of probe gases is supplied to the MSS to obtain an output signal as a response to the probe gas, the probe gas is switched to a next one, the next cycle is started, and a similar measurement is performed. By repeating such a cycle, a set of output signals for a plurality of kinds of probe gases can be obtained, and subsequent analysis can be performed. In this case, when an influence of a probe gas used in the previous cycle may remain, in order to remove or reduce the remaining probe gas, a purging treatment such as keeping the MSS in a purge gas flow for a sufficient time is preferably performed between cycles. This is because it is preferable to minimize a change in the MSS (specifically, the receptor on the MSS) caused by the previous cycle after the purging treatment in order to facilitate analysis of an output signal. From this point of view, it can be said that a combination of receptor-liquid sample component-purge gas that gives the receptor an irreversible change that affects an output signal of the MSS may be unfavorable. Alternatively, even when an irreversible change occurs in the receptor to affect an output signal, by preventing such an influence from causing a substantial influence on final results of identification, quantification, and the like by performing a post-treatment or the like, an adverse influence of the irreversible change can also be cancelled. On the contrary, pattern recognition or the like can also be performed by using even the influence of the irreversible change on the output signal as features of the output signal.

In analysis using the MSS, a process of obtaining saw-tooth-shaped output signals by switching between a sample gas and a purge gas at a predetermined cycle in each cycle and analyzing the output signals is usually adopted. It is preferable to follow such a method for performing periodic switching also in the present invention. A probe gas (corresponding to the above-described sample gas) used for the above switching in a cycle may be the same as or different from a probe gas used between cycles. Furthermore, the purging treatment may be performed by using a liquid such as water instead of using the purging gas between cycles. Note that use of a liquid for cleaning a gas sensor is described in Patent Literature 2, and therefore refer to Patent Literature 2 as necessary. In the case of the purging treatment using a liquid, the liquid adhering to the MSS may be removed by, for example, drying the liquid as necessary before a cycle using a next probe gas starts.

Therefore, from the output signals obtained in this way, it is possible to identify or quantify various components in the liquid sample and a combination thereof. Instead of identifying and quantifying individual components in the liquid sample, it is also possible to identify what the liquid sample itself is even when the individual components are unknown. For example, in the following Example, an example of determining whether a liquid sample is water, a serum-free medium, or a serum-containing medium is described.

In a simple situation, for example, when it is known that the kinds of components that may be present in a liquid sample are limited to one or a very limited number, or when a very characteristic response signal pattern specific to a particular substance is detected, as described above, a result of liquid sample analysis can be immediately obtained by visual observation of the response signal pattern or the like. However, in many cases, liquid sample analysis can also be performed, as described above, for example, by subjecting response signals to pattern recognition using various statistical processes such as multivariate analysis including PCA and LDA, or machine learning.

Examples of a material that can be used as the receptor include various polymers, various organic and inorganic compounds and single substance materials other than the polymers, porous materials, particle aggregates, and many other receptor materials that can be used for gas analysis. A specific material to be used may be appropriately selected depending on a liquid sample to be analyzed and the type of probe gas used in the second half of the measurement process. A response signal from the MSS indicates various patterns depending on a combination of a liquid sample (component in the liquid sample), a receptor, and a probe gas. Many liquid samples that can be analyzed each have a complicated composition containing a large number of components. However, by supplying appropriately selected probe gases to a plurality of channels coated with different receptors, a set of detection signals containing a large amount of information regarding the kinds of components (and their amounts) in a liquid sample that is being measured is obtained. Therefore, even for a liquid sample having a complicated composition, high-accuracy and high-speed liquid sample analysis can be achieved using a relatively simple apparatus configuration by appropriately selecting a receptor and a probe gas and performing an appropriate treatment on the resulting set of detection signals. As a matter of course, water vapor, ethanol, heptane, and toluene were used in Example as a probe gas, but the probe gas is not limited thereto. One or more appropriate gases, a mixed gas obtained by mixing any kinds of gases, or the like can be appropriately selected as a probe gas depending on a combination of a sample to be measured (or a component that is desirably detected or expected to be detected), a receptor, and other conditions.

Note that an apparatus having a configuration in which the same type of probe gas is supplied to all channels in the second half of the measurement process described above simplifies the structure and control of a gas flow path in the apparatus. On the contrary, when different kinds of probe gases between channels can be supplied, the structure and control of a gas flow path are complicated, but ability to distinguish a liquid sample (or a component thereof) can be maximized.

Note that a measurement in a liquid is performed using a chemical sensor such as a surface stress sensor in some cases. However, in these cases, the measurement in a liquid is consistently performed. It can be said that the present invention is based on a technical idea completely different from prior art in that a sensor output is obtained by once extracting a component of a liquid sample from the liquid sample into a receptor and exposing the component to a probe gas. Due to this difference, the measurement process using a chemical sensor is divided into two processes: a process of extracting a liquid sample component with a receptor and a process of exposing the component to a probe gas for obtaining a detection output from the receptor containing the component by extraction. Therefore, these processes can be individually optimized, for example, by appropriately selecting suitable materials (a receptor, a gas, and other conditions) for each of the processes. In this way, since the number of controllable parameters is larger than that in a conventional measurement consistently performed in a liquid, the degree of freedom of optimization such as improvement and control of sensitivity and component selectivity is improved.

EXAMPLE

Hereinafter, the present invention will be described in more detail based on Example. It should be noted that the following Examples are examples to make the present invention easily understood and does not limit the present invention to any particular embodiment.

Experiment 1—a Receptor Material is Distinguished Using MSS from a Known Probe Gas Contrary to Conventional Gas Analysis In this experiment, an MSS coated with four kinds of receptor materials, that is, polystyrene (PS), poly(4-methylstyrene) (P4MS), polycaprolactone (PCL), and polyvinylidene fluoride (PVF) was prepared. To these receptor materials, four kinds of probe gases, that is, water vapor, ethanol, n-heptane, and toluene were supplied to obtain output signals. The chemical structural formulas of the above four kinds of receptor materials are illustrated below.

[Chemical Formula 1]

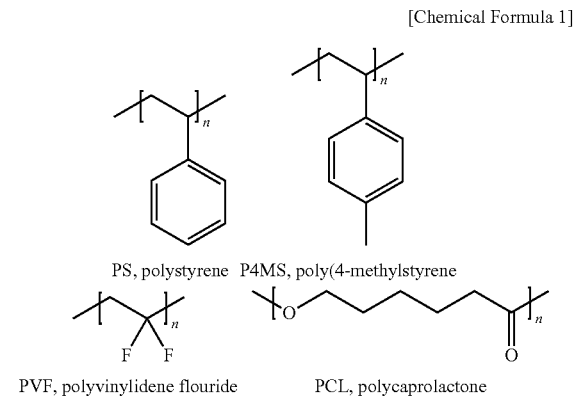

PS, polystyrene  P4MS, poly(4-methylstyrene)

PVF, polyvinylidene flouride  PCL, polycaprolactone

The four kinds of polymers used as receptor materials, PS (Mw=350,000), PCL, P4MS, and PVF were purchased from Sigma-Aldrich. N,N'-dimethylformamide (DMF) used as a solvent for forming a membrane by inkjet by preparing a polymer solution was purchased from Fujifilm Wako Pure Chemical Industries, Ltd.

Ethanol, heptane, and toluene (analytical or higher grade) used as probe gases were purchased from Sigma-Aldrich, Tokyo Chemical Industry Co., Ltd., and Fujifilm Wako Pure Chemical Industries, Ltd. All chemicals were used as purchased. Ultrapure water was used in order to obtain water vapor (also written as water in the drawing) used as a probe gas.

Each polymer was dissolved in DMF at a concentration of 1 mg/mL, and the resulting solutions were deposited on each channel of the MSS by inkjet spotting. That is, each channel of the MSS was coated with each polymer by inkjet spotting. An inkjet spotter (LaboJet-500SP from MICROJET Corporation) equipped with a nozzle (IJHBS-300 from MICROJET Corporation) was used. The injection speed, volume of a droplet, and number of inkjet shots were fixed at about 5 m/sec, about 300 pL, and 300 shots, respectively. A stage of the inkjet spotter was heated at 80° C. to dry DMF. Each polymer was coated at least two different channels on the MSS to investigate the coating quality. The specific number of coated channels (N) was as follows: PS: N=11; PCL: N=11; P4MS: N=11; PVF: N=11.

Since all the four kinds of substances used as probe gases are liquids at room temperature, using vapor of each of the four substances as a probe gas, a detection signal indicating a gas-solid interaction was obtained for each of combinations of the four kinds of probe gases with four kinds of polymers from the MSS (more specifically, four MSS channels disposed on an MSS chip) (these substances in a liquid state may be hereinafter referred to as solvents or solvent liquids). Specifically, the following apparatus configuration and procedure were used.

The polymer-coated MSS chips prepared as described above were mounted in a Teflon (registered trademark) chamber (MSS chamber), which was placed in an incubator with controlled temperature of 25.0±0.5° C. The chamber was connected to a gas system consisting of: two mass flow controllers (MFC (MFC-1 and MFC-2)); a purging gas line; a mixing chamber and a vial for a solvent liquid in an incubator with a controlled temperature of 15.0±0.5° C. The vapor of each solvent was produced by bubbling of a carrier gas supplied through MFC-1. Pure nitrogen gas was used as a carrier gas and a purge gas. The total flow rate was kept at 100 mL/min during the experiments. The concentrations of the four different kinds of solvent vapors were controlled using MFC-1 at Pa/Po=0.1, where Pa and Po stand for the solvent's partial vapor pressure and saturated vapor pressure, respectively.

Figure 2:
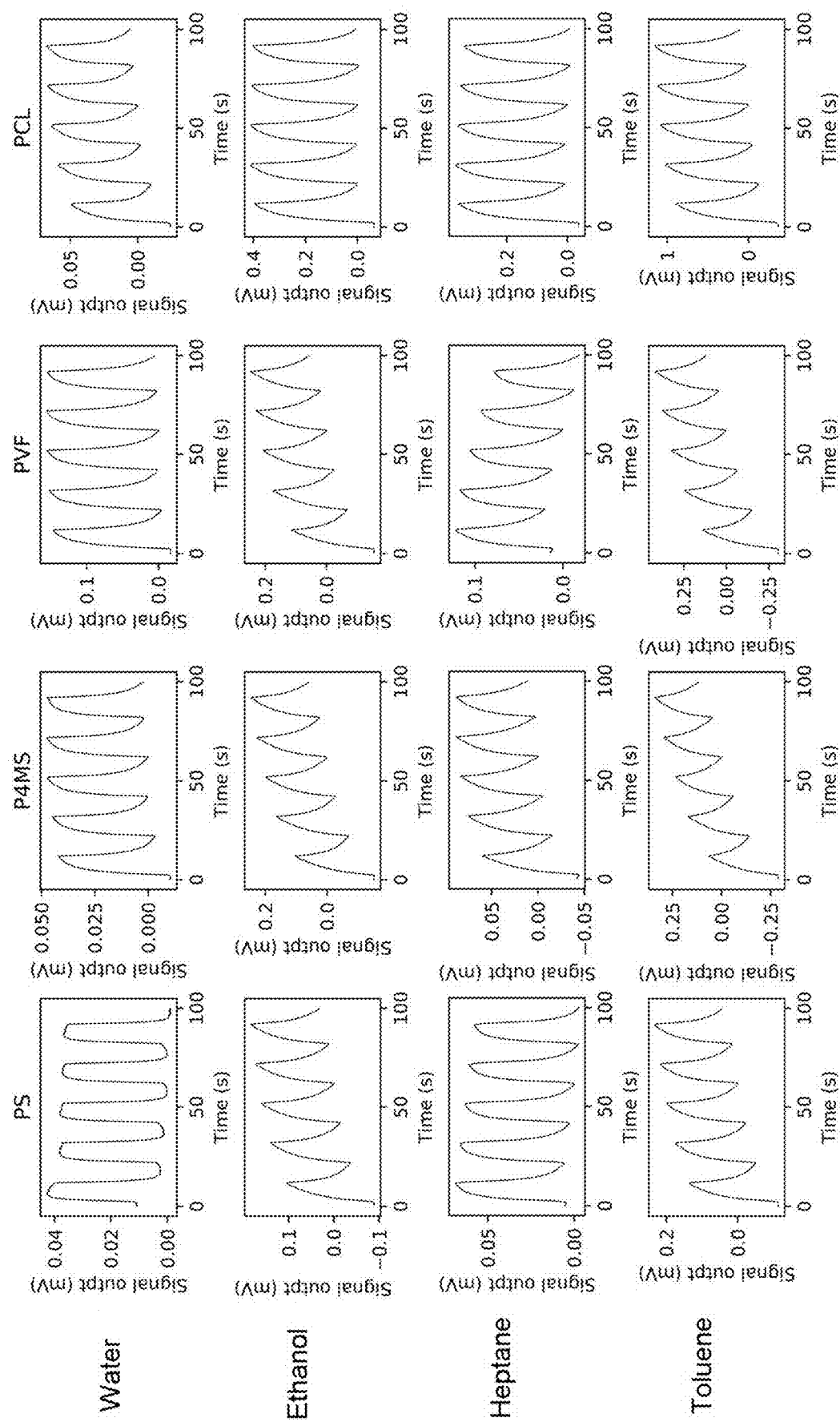
FIG. 2 presents graphs illustrating examples of output signals obtained for each of combinations of four kinds of probe gases with MSS channels coated with four kinds of polymers, PS, P4MS, PVF, and PCL in Example of the present invention.

Before measuring MSS signals, pure nitrogen gas was introduced into the MSS chamber for one minute from a purge gas line whose flow rate was controlled by MFC-2. Subsequently, MFC-1 (probe gas line) was switched on/off every 10 seconds with a controlled total flow rate of 100 mL/min using MFC-2. This on/off switching was repeated for five cycles. FIG. 2 illustrates examples of signals from the MSS channels coated with four kinds of polymers, PS, P4MS, PVF, and PCL with respect to the four kinds of probe gases (vapors), water vapor, ethanol, heptane, and toluene. This figure illustrates specific examples of output signals corresponding to respective combinations of the MSS channels coated with the above four kinds of polymers and four kinds of probe gases. The data were measured with a bridge voltage of the MSS channels of −0.5 V and recorded with a sampling rate of 10 Hz.

As described above, when each polymer was exposed to each vapor, as can be seen from FIG. 2, a response signal from each polymer (signal output from the MSS channel) was unique in terms of intensity and shape, reflecting chemical and physical affinity between the polymer and the vapor.

Figure 3:
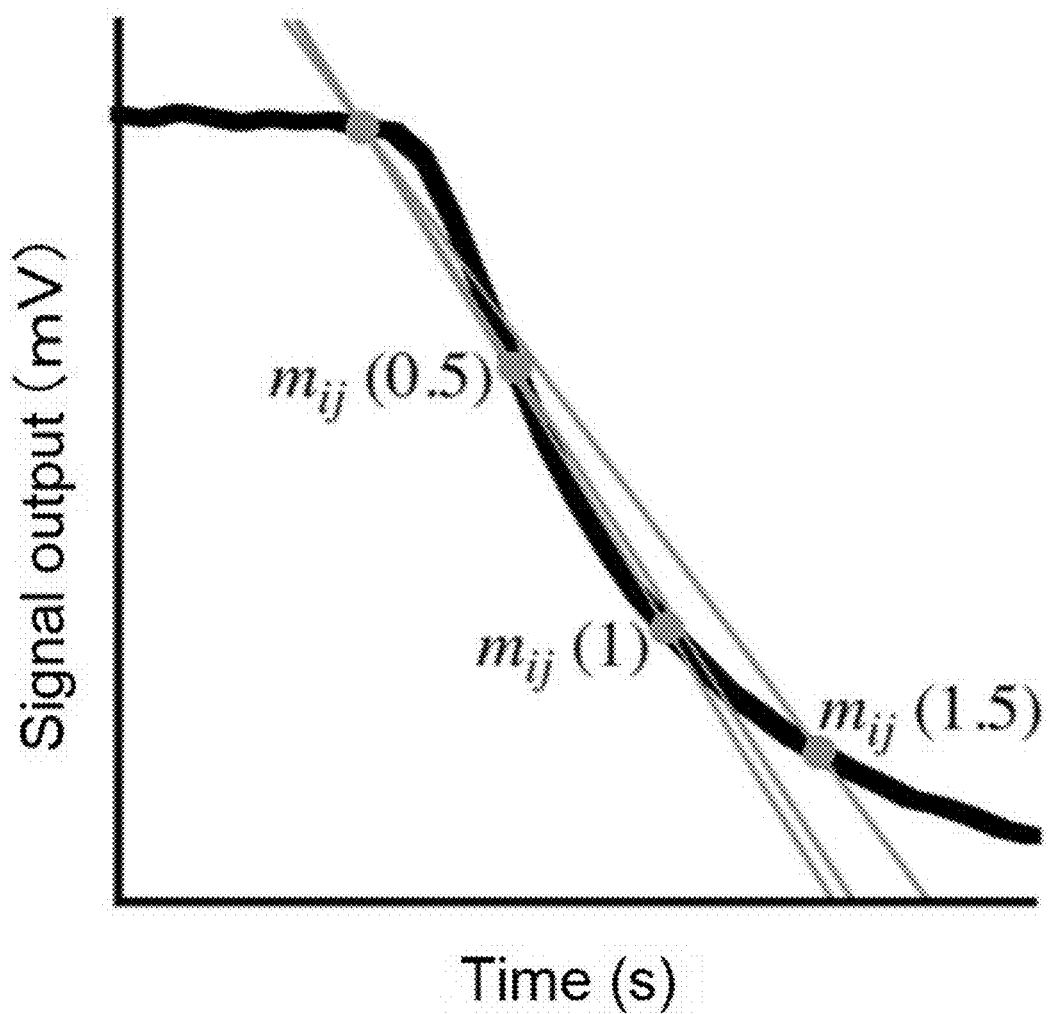
FIG. 3 is a diagram illustrating a method for extracting a feature value from a normalized output signal in Example of the present invention.
Figure 4:
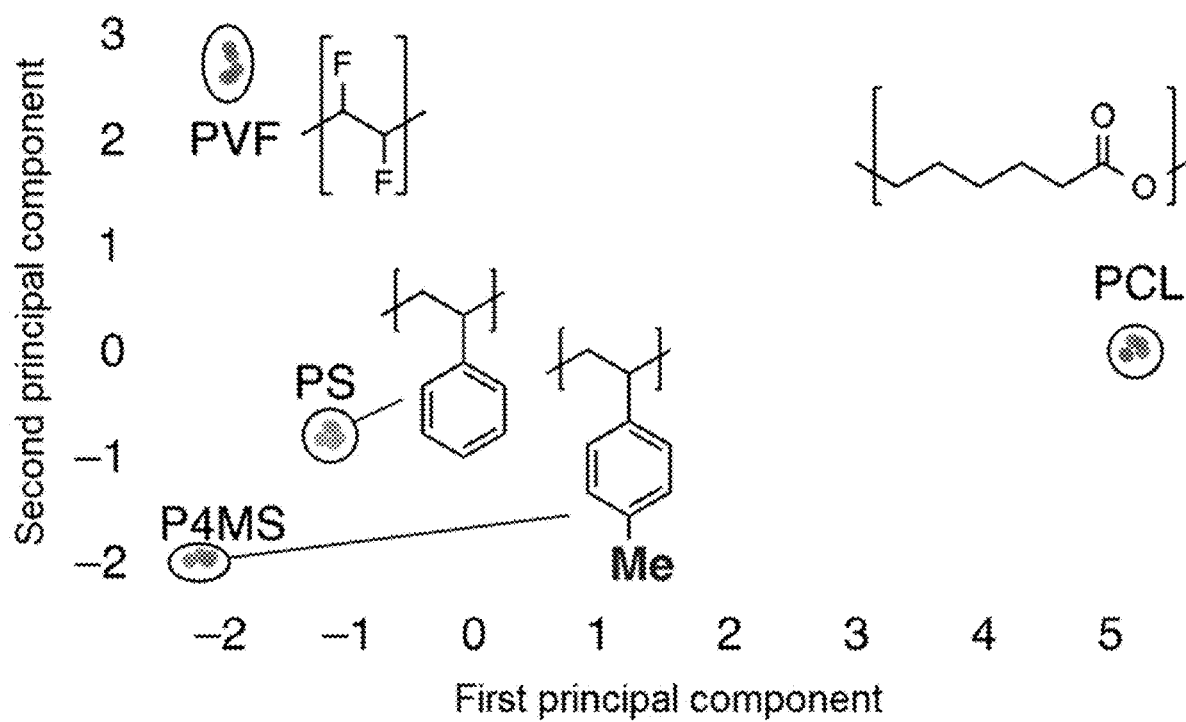
FIG. 4 is a graph of principal component analysis results illustrating results of experiments for demonstrating the principle of the present invention.

Analysis using principal component analysis (PCA) was performed for the datasets thus obtained (that is, sets of data obtained by digitizing the waveform of each response signal). As illustrated in FIG. 3, a plurality of parameters was extracted as a set of the feature values from each decay curve of each normalized response signals. More specifically, as output signals from the MSS channels coated with any one of P4MS, PCL, PS, and PVF, four series of output signals were obtained when water vapor, ethanol, heptane, and toluene were supplied as probe gases. A set of the four series of output signals was used as one data set for a corresponding receptor material. The four data sets corresponding to the four kinds of receptor materials were subjected to principal component analysis. Results thereof are illustrated in FIG. 4. In FIG. 4, the plots for the receptor materials P4MS, PCL, PS, and PVF are grouped in narrow regions that do not overlap each other, respectively. Near these regions, the abbreviations of receptor materials corresponding to these regions are attached, and the chemical structural formulas of the receptor materials are indicated.

From the above example, contrary to prior art, it has been demonstrated that a receptor material can be identified by pattern recognition (PCA in this Example) from a response signal on a receptor side to a gas (probe gas in this case) supplied to the MSS for analysis. More specifically, in Experiment 1 above, four kinds of polymers, which are known materials, were distinguished, but of course, this method is not limited to verification of a known material. That is, the receptor on the MSS into which a specimen (component to be measured) in a sample is taken by adsorption or the like through a treatment such as immersion in a sample liquid has become a material different from the receptor before immersion, and therefore is an unknown receptor. According to this experiment, such an unknown receptor can be distinguished from another receptor (a receptor, for example, immersed in a different sample liquid, a receptor subjected to a different treatment such as immersion even if the same sample liquid is used, a "raw" receptor which has not been subjected to any treatment such as immersion, and the like) and can be determined to be a receptor belonging to a class different from these different receptors. This means that a substance adsorbed on the receptor from the sample liquid is, for example, distinguished or identified in the end.

Figure 5:
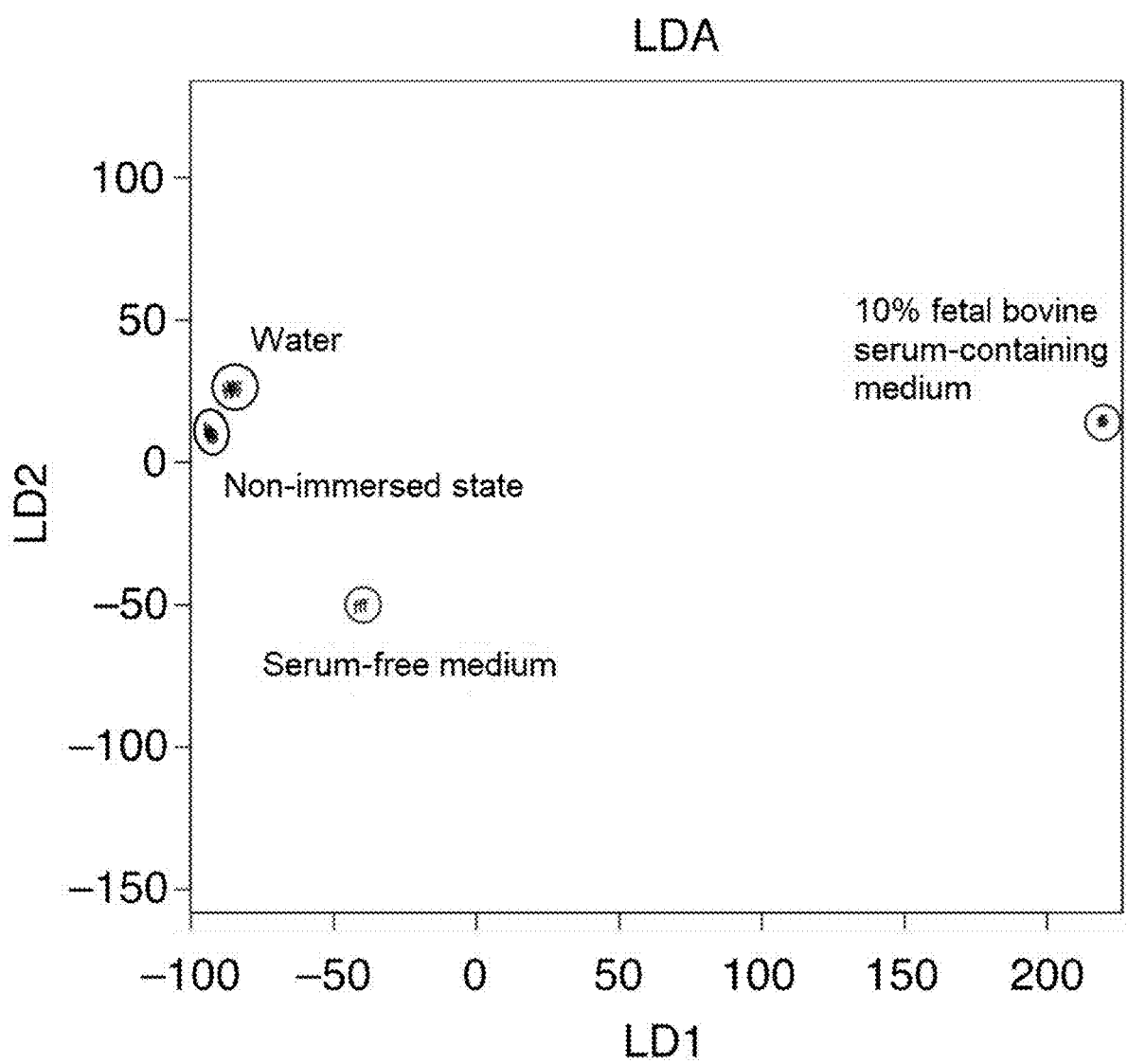
FIG. 5 is a graph illustrating results of LDA for identifying a fetal bovine serum-containing medium, a fetal bovine serum-free medium, and the like in Example of the present invention.

Experiment 2—it is Distinguished Whether a Medium is Water, a Serum-Free Medium, or a Serum-Containing Medium In this experiment, data sets were obtained from measurement signals when water vapor and ethanol were supplied as probe gases to an MSS immersed in a 10% fetal bovine serum (FBS)-containing medium or a fetal bovine serum-free medium (in which Dulbecco's modified eagle medium (DMEM) (high glucose) was used as a medium). In addition, data sets were also obtained when the same MSS was immersed in water and then the same probe gas was supplied thereto, and when the same probe gas was supplied to an MSS that had just been coated with a receptor and had not been immersed in water, a serum-containing medium, or a serum-free medium (hereinafter, this state is referred to as a non-immersed state). The specific procedure for obtaining these data sets was similar to that in Experiment 1. In the actual experimental procedure, two MSS chips were prepared, and for each of a serum-containing medium and a serum-free medium, the MSS was first coated with a receptor, and then measured without being immersed in anything (that is, in a non-immersed state), then immersed in water and measured, and furthermore, the same MSS was immersed in the media (one MSS was immersed in the serum-containing medium, and the other MSS was immersed in the serum-free medium) and measured. FIG. 5 illustrates plots of results of LDA for the above four kinds of data sets. Note that an object of this experiment is to distinguish between three types: water, an aqueous solution of medium containing a serum, and an aqueous solution of a serum-free medium. A reason why two MSS chips are used in this experiment is as follows. That is, once an MSS chip is immersed in an aqueous solution of medium containing a serum or an aqueous solution of a serum-free medium, it is not necessarily possible to sufficiently clean the MSS chip such that an influence of such medium components does not remain in the receptor on the MSS chip. Therefore, when the same MSS is immersed subsequently in the other aqueous solution (an aqueous solution of a serum-free medium or an aqueous solution of medium containing a serum), inaccurate results may be obtained. In addition, a reason why the MSS chip is immersed in water is as follows. That is, in this case, it is considered that even when a measurement with an aqueous solution of medium containing a serum or an aqueous solution of a serum-free medium is performed subsequently using the same MSS, an influence of the first water immersion does not remain due to cleaning after the measurement, and that a solid component or the like dissolved does not remain.

In FIG. 5, plot results for the fetal bovine serum-containing medium, the fetal bovine serum-free medium, water, and non-immersed state are contained in regions that are clearly separated from each other, respectively. Therefore, according to the present invention, it is possible to identify a liquid sample as to whether the liquid sample is a fetal bovine serum-containing medium, a fetal bovine serum-free medium, or water. Alternatively, it is possible to discriminate whether a measurement has been performed on an MSS that has not been, for example, immersed in a liquid sample and has been simply coated with a receptor as a comparison target or for verification of normal operation of an apparatus (or by some kind of erroneous operation).

INDUSTRIAL APPLICABILITY

As described in detail above, according to the present invention, the treatment of the second half in the liquid sample analysis for directly obtaining measurement data can be implemented by using a gas measurement method using a chemical sensor represented by MSS, as it is, the gas measurement method having many advantages as compared with liquid measurement and having many findings, data, and the like accumulated so far. Therefore, the present invention is expected to largely contribute to liquid sample analysis.

CITATION LIST

Patent Literature

Patent Literature 1: WO 2011/148774 A
Patent Literature 2: WO 2018/079509 A

Non Patent Literature

Non Patent Literature 1: G. Yoshikawa, T. Akiyama, F. Loizeau, K. Shiba, S. Gautsch, T. Nakayama, P. Vettiger, N. Rooij and M. Aono. Sensors, 2012, 12, 15873-15887.

The invention claimed is:

1. A method for analyzing a liquid sample, the method comprising,
providing a chemical sensor with a receptor layer supported thereon,
supplying the liquid sample to be measured to the chemical sensor,
supplying one or more kinds of gases to the chemical sensor after supplying the liquid sample, and
analyzing a component in the liquid sample to be measured based on a signal output from the chemical sensor exerted by a change in a physical parameter due to supply of the one or more kinds of gases to the chemical sensor.

2. The method for analyzing a liquid sample according to claim 1, wherein the receptor layer is dried before the one or more kinds of gases are supplied to the chemical sensor.

3. The method for analyzing a liquid sample according to claim 1, wherein the physical parameter is one or more selected from a group consisting of surface stress, stress, force, surface tension, pressure, mass, elasticity, Young's modulus, Poisson's ratio, resonance frequency, frequency, volume, thickness, viscosity, density, magnetic force, magnetic quantity, magnetic field, magnetic flux, magnetic flux density, electric resistance, electric quantity, dielectric constant, electric power, electric field, charge, current, voltage, potential, mobility, electrostatic energy, capacitance, inductance, reactance, susceptance, admittance, impedance, conductance, plasmon, refractive index, luminous intensity, and temperature.

4. The method for analyzing a liquid sample according to claim 3, wherein the physical parameter is surface stress.

5. The method for analyzing a liquid sample according to claim 4, wherein the chemical sensor is a membrane-type surface stress sensor.

6. The method for analyzing a liquid sample according to claim 1, wherein the receptor layer comprises a material selected from a group consisting of a polymer, an organic compound other than the polymer, an inorganic compound, a simple substance material, a porous body, and an aggregate of particles.

7. The method for analyzing a liquid sample according to claim 1, wherein the analysis is performed based on a result of extracting a feature value from the signal output from the chemical sensor.

8. The method for analyzing a liquid sample according to claim 1, wherein the gas and a purging fluid are alternately supplied to the chemical sensor.

9. The method for analyzing a liquid sample according to claim 1, wherein the component in the liquid sample to be measured is analyzed by subjecting the signal output from the chemical sensor to machine learning.

10. The method for analyzing a liquid sample according to claim 1, wherein the component in the liquid sample to be measured is analyzed by subjecting the signal output from the chemical sensor to multivariate analysis.

11. The method for analyzing a liquid sample according to claim 10, wherein the component in the liquid sample to be measured is analyzed by applying principal component analysis or linear discriminant analysis to the signal output from the chemical sensor.

12. The method for analyzing a liquid sample according to claim 10, wherein the component in the liquid sample to be measured is analyzed by applying pattern recognition to the signal output from the chemical sensor.

13. An apparatus for analyzing a liquid sample comprising a chemical sensor, and means for analysis that analyzes a signal output from the chemical sensor so that the apparatus for analyzing a liquid sample performs the method for analyzing a liquid sample according to claim 1.

* * * * *